US011925194B2

(12) United States Patent
Langer et al.

(10) Patent No.: US 11,925,194 B2
(45) Date of Patent: Mar. 12, 2024

(54) ANTIMICROBIALLY ACTIVE MIXTURES

(71) Applicant: SYMRISE AG, Holzminden (DE)

(72) Inventors: Kathrin Langer, Dassel-Hilwartshausen (DE); Margit Liebig, Stadtoldendorf (DE); Johannes Kiefl, Holzminden (DE)

(73) Assignee: SYMRISE AG, Holzminden (DE)

( * ) Notice: Subject to any disclaimer, the term of this patent is extended or adjusted under 35 U.S.C. 154(b) by 382 days.

(21) Appl. No.: 16/762,957

(22) PCT Filed: Nov. 14, 2017

(86) PCT No.: PCT/EP2017/079115
§ 371 (c)(1),
(2) Date: May 11, 2020

(87) PCT Pub. No.: WO2019/096363
PCT Pub. Date: May 23, 2019

(65) Prior Publication Data
US 2020/0397026 A1    Dec. 24, 2020

(51) Int. Cl.
*A23L 3/3472* (2006.01)
*A23L 27/00* (2016.01)
*A23L 27/10* (2016.01)
*A23L 27/20* (2016.01)
*A61K 36/45* (2006.01)
*A61K 36/73* (2006.01)
*A61K 36/87* (2006.01)

(52) U.S. Cl.
CPC ............. *A23L 3/3472* (2013.01); *A23L 27/10* (2016.08); *A23L 27/2028* (2016.08); *A23L 27/2052* (2016.08); *A23L 27/84* (2016.08); *A23L 27/88* (2016.08); *A61K 36/45* (2013.01); *A61K 36/73* (2013.01); *A61K 36/87* (2013.01)

(58) Field of Classification Search
CPC ........ A23L 3/3472; A23L 27/88; A23L 27/10; A23L 27/2028; A23L 27/84; A23L 27/2052; A61K 36/45; A61K 36/73; A61K 36/87
See application file for complete search history.

(56) References Cited

U.S. PATENT DOCUMENTS

| 2002/0188019 | A1 | 12/2002 | Ley et al. | |
|---|---|---|---|---|
| 2010/0284985 | A1 | 11/2010 | Mygind et al. | |
| 2011/0059205 | A1* | 3/2011 | Gaysinsky | A61K 8/498 426/597 |
| 2014/0309294 | A1* | 10/2014 | Erfurt | A23L 3/3517 426/321 |
| 2015/0328258 | A1* | 11/2015 | Evans | A61K 36/185 424/616 |
| 2017/0135982 | A1 | 5/2017 | Somoza et al. | |

FOREIGN PATENT DOCUMENTS

| AU | 2011213719 A1 | 3/2013 |
|---|---|---|
| CN | 103391774 A | 11/2013 |
| CN | 103957732 A | 7/2014 |
| CN | 104543668 A | 4/2015 |
| CN | 105284928 A | 2/2016 |
| CN | 105613709 A * | 6/2016 |
| EP | 2868209 A1 | 5/2015 |
| JP | H09266767 A | 10/1997 |
| JP | 2002360188 A | 12/2002 |
| JP | 2005068014 A | 3/2005 |
| JP | 2005154323 A | 6/2005 |
| JP | 2006505501 A | 2/2006 |
| JP | 2008502656 A | 1/2008 |
| JP | 2014129299 A | 7/2014 |
| JP | 2017523183 A | 8/2017 |

OTHER PUBLICATIONS

L. B. Hanbali, R. M. Ghadieh, et al. "The Antimicrobial Activity of Black Sour Cherry (*Prunus cerasus* L.) Extracts: I. Measurement of Sensitivity and Attenuation of Gram-Positive and Gram-Negative Bacteria and C. albicans in Culture," Curr. Nutr. Food Sci., 2013; 9: 201-216. (Year: 2013).*
Sheng Wu and Li Tian. Diverse Phytochemicals and Bioactivities in the Ancient Fruit and Modern Functional Food Pomegranate (*Punica granatum*), Molecules 2017, 22, 1606, 1-17. (Year: 2017).*
Machine translation of CN-105613709-A from EPO (Year: 2022).*
P. E. Shaw and R. L. Coleman. "Quantitative Composition of Cold-Pressed Orange Oils," J. Agr. Food Chem., vol. 22, No. 5, 1974, 785-787. (Year: 1974).*
S.M. Omran, et al. "The Effects of Limonene and Orange Peel Extracts on Some Spoilage Fungi," International Journal of Molecular and Clinical Microbiology 1 (2011) 82-86. (Year: 2011).*
Ngaldi. "Veggie Burgers with Pomegranate Ketchup," downloaded Dec. 15, 2022 from https://www.keyingredient.com/recipes/271527794/veggie-burgers-with-pomegranate-ketchup/, dated 2014. (Year: 2014).*
G.K. Jayaprakasha, et al. Antimicrobial Activities of Pomegranate, Chapter 11 of Pomegranates: Ancient Roots to Modern Medicine, Edited By David Heber, Risa N. Schulman, Navindra P. Seeram; 1st Edition, First Published 2006; eBook Published Jul. 6, 2006; Boca Raton Imprint, CRC Press, pp. 167-183. (Year: 2006).*
F. Les, et al. "Pomegranate juice and its main polyphenols exhibit direct effects on amine oxidases from human adipose tissue and inhibit lipid metabolism in adipocytes," Journal of Functional Foods, vol. 33, 2017, pp. 323-331. (Year: 2017).*
C. Ravichandran, et al. "Review of toxicological assessment of d-limonene, a food and cosmetics additive," Food and Chemical Toxicology 120 (2018) 668-680. (Year: 2018).*
A. Thakre, et al. "Limonene inhibits Candida albicans growth by inducing apoptosis," Medical Mycology, 2018, 56, 565-578. (Year: 2018).*

(Continued)

*Primary Examiner* — Michael P Cohen
(74) *Attorney, Agent, or Firm* — POLSINELLI PC

(57) ABSTRACT

The present invention is on the field of antimicrobial active substances. In addition to novel uses of distinct antimicrobial mixtures according to the invention, the present invention also relates to preparations containing such mixtures, particularly preparations serving for nutrition or pleasure or pharmaceutical preparations, as well as methods for preparing such preparations and methods for antimicrobial treatment of preparations serving for nutrition or pleasure or pharmaceutical preparations.

17 Claims, No Drawings

(56) References Cited

OTHER PUBLICATIONS

A. A. Tayel and W. F. El-Tras. "Anticandidal activity of pomegranate peel extract aerosol as an applicable sanitizing method," Mycoses 53, 2009, 117-122. (Year: 2009).*
Japanese Office Action dated May 9, 2022 for corresponding Japanese Application No. 2020-526476.
Endo, E. H. et al., "Potent antifungal activity of extracts and pure compound isolated from pomegranate peels and synergism with fluconazole against Candida albicans," Institut Pasteur, Research in Microbiology, vol. 161, 2010, pp. 534-540.
Hadrich, F. et al., "Antioxidant and Lipase Inhibitory Activities and Essential Oil Composition of Pomegranate Peel Extracts," Journal of Oleo Science, vol. 63, No. 5, 2014, pp. 515-525.
Jeong, Ki-Woong et al., "Screening of Flavonoids as Candidate Antibiotics against Enterococcus faecalis," J. Nat. Prod., vol. 72, 2009, pp. 719-724.
Andrade Lopes, L. A. et al., "Inhibitory effects of flavonoids on biofilm formation by *Staphylococcus aureus* that overexpresses efflux protein genes," Microbial Pathogenesis, vol. 107, 2017, pp. 193-197.
Reddy, S. V. et al., "Antibacterial constituents from the berries of Piper nigrum," Phytomedicine, vol. 11, 2004, pp. 697-700.
Delaquis, P. et al., "Effect of pH on the Inhibition of *Listeria* spp. by Vanillin and Vanillic Acid," Journal of Food Protection, vol. 68, No. 7, 2005, pp. 1472-1476.
Patel, K. D. et al., "Proanthocyanidin-rich Extracts from Cranberry Fruit (*Vaccinium macrocarpon* Ait.) Selectively Inhibit the Growth of Human Pathogenic Fungi *Candida* spp. and Cryptococcus neoformans," Journal of Agricultural and Food Chemistry, vol. 59, 2011, pp. 12864-12873.
Grace, M. H. et al., "Comparative Analysis of Phenolic Content and Profile, Antioxidant Capacity, and Anti-inflammatory Bioactivity in Wild Alaskan and Commercial Vaccinium Berries," Journal of Agricultural and Food Chemistry, vol. 62, 2014, pp. 4007-4017.
Lacombe, A. et al., "The antimicrobial properties of the lowbush blueberry (*Vaccinium angustifolium*) fractional components against foodborne pathogens and the conservation of probiotic Lactobacillus rhamnosus," Food Microbiology, vol. 30, 2012, pp. 124-131.
Han, Y., "Synergic effect of grape seed extract with amphotericin B against disseminated candidiasis due to Candida albicans," Phytomedicine, vol. 14, 2007, pp. 733-738.
Guendez, R. et al., "An Analytical Survey of the Polyphenols of Seeds of Varieties of Grape (*Vitis vinifera*) Cultivated in Greece: Implications for Exploitation as a Source of Value-added Phytochemicals," Phytochemical Analysis, vol. 16, 2005, pp. 17-23.
International Search Report and Written Opinion dated Sep. 28, 2018 for corresponding PCT Application No. PCT/EP2017/079115.
Osman Sagdic et al., "Effect of Grape Pomace Extracts Obtained from Different Grape Varieties on Microbial Quality of Beef Patty," Journal of Food Science, vol. 76, No. 7, 2011, pp. M515-M521.
Ivica Dimkic et al., "Phenolic profiles and antimicrobial activity of various plant resins as potential botanical sources of Serbian propolis," Industrial Crops and Products, vol. 94, 2016, pp. 856-871.
R. Puupponen-Pimia et al., "Antimicrobial properties of phenolic compounds from berries," Journal of Applied Microbiology, vol. 90, No. 4, 2001, pp. 494-507.
Sh. Abdollahzadeh et al., "Antibacterial and Antifungal Activities of Punica Granatum Peel Extracts Against Oral Pathogens," Journal of Dentistry, 2011, pp. 1-6.
Japanese Office Action dated Sep. 27, 2021 for corresponding Japanese Application No. 2020-526476.
Osman Sagdic et al., "Effect of Grape Pomace Extracts Obtained from Different Grape Varieties on Microbial Quality of Beef Patty," Journal of Food Science, vol. 76, No. 7, 2011, pp. 515-521.
Chinese Office Action dated Sep. 14, 2022 for corresponding CN Application No. 201780096745.4.

* cited by examiner

ANTIMICROBIALLY ACTIVE MIXTURES

CROSS-REFERENCE TO RELATED APPLICATIONS

This application is a national stage application (under 35 U.S.C. § 371) of PCT/EP2017/079115, filed Nov. 14, 2017, which is incorporated herein by reference in its entirety.

The present invention is on the field of antimicrobial active substances. In addition to novel uses of distinct antimicrobial mixtures according to the invention, the present invention also relates to preparations containing such mixtures, particularly preparations serving for nutrition or pleasure or pharmaceutical preparations, as well as methods for preparing such preparations and methods for antimicrobial treatment of preparations serving for nutrition or pleasure or pharmaceutical preparations. Further aspects of the present invention result from the subsequent descriptions and particularly the attached patent claims.

Foodstuffs, particularly with ingredients of animal origin (such as mayonnaise, minced meat and sausage products) as well as sugar containing foodstuffs (such as sweetened drinks, syrups, ketchup and dressings) are prone to microbial decay due to their richness in nutrients and high water activity coefficients (aw-value).

For stabilizing such products, typically the concept of hurdles is applied [Kramer, J., Alexander, P. (2017). Lebensmittel-Mikrobiologie. Stuttgart, publisher Eugen Ulmer. 7., completely reviewed edition.]: Raw materials with a low initial germination number are selected, the aw-value, the redox potential and the pH value are reduced, if possible, when formulating the products and when processing the products, particular attention is paid on food hygiene and good manufacturing practice. As the last hurdle, methods of preservation, such as pasteurization or the use of preservatives, are applied. However, classical methods of preservation are increasingly considered as critical by consumers. As an example, the amount of nutrients can be reduced and the taste can be impaired by forming cooked notes by pasteurization. Preservatives such as sorbic acid and benzoic acid are obtained synthetically and need to be declared as additives. Natural preservatives such as acidic acid, mustard seeds, essential oils and extracts thereof can only be applied in certain limits, as these strongly change the product in a sensorial manner.

While the growth of bacteria is strongly inhibited by a pH-value smaller than 4.5, with the exception of acidophilic bacteria such as *Lactobacillus* sp. or *Acetobacter* sp., yeasts and fungi can also grow at pH-values smaller than 3 and lead to decay. Special yeasts such as *Zygosaccharomyces* baili, *Zygosaccharomyces lentus* and *Saccharomyces cerevisiae* also show a tolerance towards preservatives such as sorbic acid and benzoic acid [Steels, H., James, S. A., Roberts, I. N. and Stratford, M. (1999). "*Zygosaccharomyces lentus*: a significant new osmophilic, preservative-resistant spoilage yeast, capable of growth at low temperature." Journal of Applied Microbiology 87(4): 520-527. Juvonen, R., Virkajärvi, V., Priha, O. and Laitila, A. (2011) "Microbiological spoilage and safety risks in non-beer beverages." VTT Tiedotteita—Research notes 2599]. Although the decay of a foodstuff by yeasts and fungi is the most difficult to control, it is predominantly the antibacterial effect of plant extracts which is known [Friedman, M. (2015). "Antibiotic-resistant bacteria: prevalence in food and inactivation by food-compatible compounds and plant extracts." J Agric Food Chem 63(15): 3805-3822]. For example, herbs, spices and the essential oils and extracts obtained therefrom have a documented effect against bacteria [Weber, H. (2010). Mikrobiologie der Lebensmittel—Grundlagen. Hamburg, Behrs Verlag], however, these change the taste in an inacceptable manner in many products due to their own aroma. Only little plant extracts with an antimicrobial effect against yeasts and fungi are known and their use in foodstuff is often limited due to their own aroma, strongly colouring characteristics and low solubility.

Therefore, it was an aim and primary object of the present invention, to develop alternative formulations for prolonging the durability of a perishable foodstuff without undue technological effort, preferably by addition of plant based natural ingredients, and thereby preferably not to negatively impact or ideally even round or, respectively, improve the taste.

Additionally, the formulations to be provided should be toxicologically harmless, highly compatible, stable (particularly in typical formulations) and/or be inexpensively producible.

It is further desirable if as less of the antimicrobial active substances as possible has to be used in the respective formulations for achieving a certain antimicrobial effect.

The search for suitable substances which have one or more of the mentioned characteristics in a sufficient amount is additionally complicated for the skilled person by that no clear dependency between the chemical structure of a substance on the one side and its biological activity towards certain microorganisms (germs) as well as its stability exists. Furthermore, there is no predictable connection between the antimicrobial effect, the toxicological harmlessness and the stability of a substance.

The preferred object of the present invention was thus to provide formulations which fulfil several or preferably all of the above criteria or which have a desirable combination of the above characteristics.

The primary object is solved by the use of a mixture comprising or consisting of (A) one or more plant extract(s) with antimicrobial effect and/or one or more fraction(s) thereof with antimicrobial effect,
   selected from the group consisting of extracts
   of plants of the following families: Asparagaceae, Cannabaceae, Ericaceae, Lythraceae, Krameriaceae, Rosaceae, and Vitaceae
   preferably of the following plants: *Humulus lupulus, Fragaria×anapassa, Krameria lappacea, Punica granatum, Vaccinium angustifolium, Vaccinium macrocarpon, Vaccinium myrtillus, Vaccinium vitis-idaea, Vitis vinifera*,
   and fractions thereof,
and
(B) one or more flavouring agent(s) with antimicrobial effect and/or which increase the antimicrobial efficacy of component (A) and/or which reduce, mask or modify an unpleasant taste impression of component (A) and/or which increase or modify a pleasant taste impression of component (A),
   selected from the group consisting of Abrusosides and Balansines (preferably as described in WO 2012 164,062), malic acid, Benzaldehyde, gammaDecalacton, delta-Decalacton, 3,7'-Dihydroxy-4'-methoxyflavan-isomeres (preferably as described in EP 2,253,226), Eriodictyol, Ethyl-2-methylbutyrat, Ethylbutyrate, Ethylcapronate, Geranial, Hesperetin (preferably as described in WO 2007/014879, EP 2,368,442-B1 or EP 1,909,599-B1), or extracts of *Rubus suavissimus* (preferably as described in U.S.

Provisional Application 61/333,435 and the patent application based thereon), Hesperetindihydrochalkone, Hesperidindihydrochalkone, Hydroxybenzoic acid amides (preferably as described in WO 2006/024587) for example 2,4-Dihydroxybenzoic acid vanillyl amide, 4-Hydroxydihydrochalcone (preferably as described in US 2008/0227867 A1 and WO 2007/107596) for example Phloretin and Davidigenin, p-Hydroxybenzaldehyde, p-Hydroxybenzoic acid, Homoeriodictyol, Limonen, lactic acid, Menthofurolacton, Mogroside, Naringenin, Naringindihydro-chalkon, Neoisoflavonoids (preferably as described in EP 2,570,036 B1), Neohesperidi ndhydrochalkon, Neral, delta-Octalacton, Pellitorin (preferably as described in EP 2 008 530 A1 or in form of aroma compositions described therein and derived therefrom), Piperonal, Phloridzin, Phyllodulcin-Isomers (preferably as described in EP 2,298,084 B1), Rubusoside (preferably as described in EP 2,386, 211), mixtures of Rubusosid-isomers and -homologues, 1-(2,4-Dihydroxy-phenyl)-3-(3-hydroxy-4-methoxy-phenyl)-propane-1-on (preferably as described in EP 2,353,403-B1), Steviosides and Rebaudiosides (preferably mixtures of different rebaudiosides, e.g. as described in WO 2015 062 998), Trilobatin, Vanillin, Vanillic acid (preferably as described in the European Patent Application with the serial number EP 2,517,574), vanillyl lignanes, tartaric acid and cinnamon aldehyde, as antimicrobial mixture, preferably as synergistic antimicrobial mixture.

According to an embodiment of the present invention, preferably the root and/or the fruiting organs of the plant or parts thereof, preferably endo-, meso-, exocarp and/or parts of the flower head are used for the one or more plant extract(s) with antimicrobial effect according to (A) and/or for the one or more fraction(s) thereof.

The substance(s) according to (B) or parts thereof may, according to an embodiment of the present invention, be present in form of an extract/in an extract or in form of a fraction thereof/in a fraction thereof, preferably selected from the group consisting of extracts (or fractions thereof) of the following plants: *Artemisia xanthochroa, Artemisia dracunculus, Bauhinia manca, Chenopodium album, Chysothamnus* ssp., *Citrus* ssp. (insbesondere *Citrus sinensis, Citrus paradisi, Citrus bergamia*), *Dracaena cinnabaria, Herba santa, Hydrangea dulcis, Lippia dulcis, Lycoris aurea, Malus domestica, Mariscus psilostachys, Momordica grosvenorii, Piper* ssp., *Stevia* ssp., *Vanilla* ssp., *Zanthoxylum rubescens*.

Preferred according to the invention is such a use as antimicrobial mixture, wherein component (B)
  improves the antimicrobial effectiveness of component (A) (synergistic antimicrobial effect, i.e. the antimicrobial effectiveness exceeds the sum of the antimicrobial effectiveness(es) of the substances with an antimicrobial effect in the mixture), which advantageously allows using low(er) amounts of substances with an antimicrobial effect in the mixture, and/or
  reduces, masks or modifies an unpleasant taste impression of component (A), and/or
  increases or modifies a pleasant taste impression of component (A).

It is thus preferred according to the invention, that component (B) is present in the mixture to be used according to the invention in a total amount which is sufficient to improve the antimicrobial effectiveness of component (A) and/or to reduce, mask or modify an unpleasant taste impression of component (A) and/or to increase or modify a pleasant taste impression of component (A).

Here, the taste impressions to be reduced, masked or modified are preferably selected from the group consisting of astringent, bitter, herbaceous, metallic, sour.

The taste impressions to be increased or modified are preferably selected from the group consisting of sweet, juicy and full-bodied.

The mixtures to be used according to the invention are excellently suitable as antimicrobial mixture of active substances for prolonging the durability of perishable compositions.

Advantageously, the mixtures to be used according to the invention also allow to fulfil the initially mentioned criteria.

Although the experts have already partly considered the antimicrobial characteristics of components described herein, there was so far no indication that especially the mixtures to be used according to the invention have the effects and advantages as described herein. Particularly surprising is a significantly improved antimicrobial effect (particularly against the germs as described herein).

The invention is based on the surprising recognition that the mixtures according to the invention show a particularly advantageous antimicrobial effect, particularly against fungi or, respectively, yeasts, particularly against one or more germs selected from the group consisting of
  *Dekkera bruxellensis, Candida albicans, Candida parapsilosis, Candida pseudointermedia, Saccharomyces cerevisiae, Saccharomycodes ludwigii, Zygo saccharomyces bailii* and *Pichia* sp.,
  *Aureobasidium* sp., *Alternaria alternata, Aspergillus brasiliensis, Aspergillus fumigatus, Cladosporium* sp., *Fusarium* sp. *Rhodotorula* sp., *Sporidiobolus* sp., *Sporobolomyces* sp., *Paecilomyces* sp. and *Penicillium* sp.

Particularly preferred—and advantageous—is thus a use according to the invention against fungi or, respectively, yeasts, preferably against one, more or all germs selected from the group consisting of *S. cerevisiae, Z. bailii, C. albicans, A. pullulans* and *A. brasiliensis*.

It is preferred according to the invention if the extract(s) of component (A) is/are selected from the group consisting of berry extracts, preferably extracts of red berries, pomegranate extracts and herb extracts.

The extracts of component (A) can be produced from whole plants, plant parts, biotechnologically altered or unaltered plant materials, wherein methods are used which are known to a skilled person, preferably solid-liquid-extractions. Furthermore, if necessary, also enrichment and concentration of selected substances can be applied after the extraction has taken place.

For example, an extraction of dried plant parts can be applied with pure or a solvent mixture of acetone, butane, butane-1-ol, butane-2-ol, cyclohexane, dinitrogen monoxide, diethyl ether, ethyl acetate, ethanol, ethylmethylketone, hexane, carbon dioxide, methanol, methyl acetate, vegetable oils, propane, propane-1-01, propane-2-ol and/or water.

Excipients as for example surface active substances, hygroscopic substances and/or salts can be added to the extraction solvents for improving the yield.

Wet plant parts can be extracted with the aid of microwave radiation, ultrasound and pulsing electrical field.

A fractionation of the extracts (production of a fraction described herein) is preferably performed by separation of undesired side-components and/or concentration of selected substances, for example by adsorption distillation chromatographic separation, fermentation, filtration, liquid-liquid extraction, membrane filtration and/or centrifugation, preferably by chromatographic separation, liquid-liquid extraction and/or membrane filtration.

After the fractionation of the extracts, the components of the respective fractions can be determined with known methods, where appropriate. The determination of the compounds with mass spectrometry, particularly LC-MS, is a preferred method.

It is particularly preferred according to the invention, if component (A) comprises at least one, two, three or more compound(s) selected from the group consisting of catechines, chlorogenic acid, p-cumaric acid, epicatechines, ellagic acid, gallic acid, caffeic acid, sinapinic acid and cinnamic acid.

Dependent on the method of fractionantion, the ratios of the concentrations particularly of the substances catechines, chlorogenic acid, p-cumaric acid, epicatechines, ellagic acid, gallic acid, caffeic acid, sinapinic acid and/or cinnamic acid to the other components can be changed by the fractionation in a targeted way. A change is thereby preferably applied in a way in which the antimicrobial effect is improved.

In a further preferred embodiment, component (B) contains at least one, two, three or more flavouring agent(s) selected from the group consisting of eriodictyol, hesperetin, homoeriodictyol, naringenin, pellitorin and vanillic acid or consists thereof.

For mixtures to be used according to the invention preferably applies that the ratio of the total amount of component (A) to the total amount of component (B) is in a range of from 1000:1 to 1:10, preferably 100:1 to 1:10, preferably in a range of from 100:1 to 1:1, preferably 10:1 to 1:1. With regard to this feature, it preferably applies that the amount(s) of potential components which can be assigned to component (A) as well as to component (B) are assigned to the total amount of component (A).

Advantageously, the mixtures as described herein are particularly suitable for use in a preparation serving for nutrition or pleasure or a pharmaceutical preparation.

Accordingly, the present invention also relates to a preparation serving for nutrition or pleasure or a pharmaceutical preparation, comprising a mixture as described herein, wherein the mixture is present in an amount sufficient to achieve an antimicrobial effect, preferably a synergistic antimicrobial effect.

What was said above to mixtures to be preferably be used according to the invention applies accordingly for preferred embodiments of the contained mixture.

Accordingly, it is preferred if the mixture is contained in an amount sufficient for achieving an antimicrobial effect, preferably a synergistic antimicrobial effect, against one or more germs selected from the group consisting of

*Dekkera bruxellensis, Candida albicans, Candida parapsilosis, Candida pseudointermedia, Saccharomyces cerevisiae, Saccharomycodes ludwigii, Zygosaccharomyces bailii* and *Pichia* sp.,

*Aureobasidium* sp., *Alternaria alternata, Aspergillus brasiliensis, Aspergillus* fumigatus, *Cladosporium* sp., *Fusarium* sp. *Rhodotorula* sp., *Sporidiobolus* sp., *Sporobolomyces* sp., *Paecilomyces* sp. and *Penicillium* sp.

It is particularly preferred if the mixture is contained in an amount sufficient to achieve an antimicrobial effect, preferably a synergistic antimicrobial effect against one, more or all germs selected from the group consisting of *S. cerevisiae, Z. bailii, C. albicans, A. pullulans* and *A. brasiliensis.*

The use of mixtures to be used according to the invention in preparations according to the invention is thereby not limited. Thus, a plurality of different preparations serving for nutrition or pleasure or pharmaceutical preparations can be considered. Particularly preferably, preparations according to the invention are foodstuffs, particularly such with ingredients of animal origin (such as mayonnaise, minced meat and sausage products) as well as sugar containing foodstuff (such as sweetened drinks, syrups, ketchup and dressings).

According to a preferred embodiment of the present invention, a mixture to be used according to the invention is thus applied in a preparation which is selected from the group consisting of foodstuffs, preferably foodstuffs with ingredients of animal origin, such as mayonnaise, minced meat and sausage products, as well as sugar containing foodstuff such as sweetened drinks, syrups, ketchup, salad creams and dressings.

A mixture to be used according to the invention can be contained e.g. in a total amount of from 3 to 0.001, preferably of from 0.5 to 0.01, particularly preferably of from 0.1 to 0.01 wt.-%, related to the total weight of the preparation.

For these purposes, a mixture to be used according to the invention can be present in form of a liquid component or powder or spray-dried product in such preparations. Thus, for example, components (A) and (B) are mixed and dissolved and added in liquid or spray-dried form. Components (A) and (B) can also be used separately and in forms different from each other. Also, the preparations according to the invention preferably further consist of components typical for such preparations. As an example, solvents or carriers can be present.

The solvents can thereby be for example water, ethanol, 1,2-propanediol, triacetin, diacetin, triethyl citrate and/or glycerine.

Advantageous carriers are for example silicon dioxide (silica acid, silica gel), carbohydrates and/or carbohydrate polymers (polysaccharides), cyclodextrins, starches, degraded starches (starch hydrolysates), chemically or physically modified starches, modified celluloses, gum *arabicum*, ghatti-gum, tragacanth, karaya, carrageenan, guar gum, locust bean gum, alginates, pectin, inulin or xanthan gum; preferred starch hydrolysates are maltodextrins and dextrins, wherein maltodextrins with DE-values in a range of from 5 to 20 are particularly preferred. It is irrelevant which plant has originally provided the starch for producing the starch hydrolysates. Suitable and easily accessible are maize-based starches as well as starches of tapioca, rice, wheat or potatoes. The carriers can also act as flow additives such as for example silicon dioxide.

One aspect of the present invention also relates to a method for producing a preparation according to the invention, comprising or consisting of the following steps:

(i) providing a mixture as described herein,
(ii) providing one or more further components suitable for consumption,
and
(iii) mixing the components provided in steps (i) and (ii).

What was said above with regard to mixtures preferably to be used according to the invention also applies for preferred embodiments of the contained mixture. The same applies accordingly for preferred embodiments of the preparations to be produced.

Particularly preferred is also a method according to the invention for antimicrobial treatment of a preparation serving for food or pleasure, preferably as described above, or a pharmaceutical preparation, comprising or consisting of the following steps:
(i) providing a mixture as described herein,
(ii) providing a preparation to be treated or one or more further components of a preparation to be treated which are suitable for consumption, and
(iii) adding the mixture to the provided preparation or, respectively, to the component(s) of the preparation which is/are suitable for consumption, in an amount sufficient for
achieving an antimicrobial effect, preferably achieving a synergistic antimicrobial effect,
preferably for achieving an antimicrobial effect, preferably for achieving a synergistic antimicrobial effect, against one or more germs selected from the group consisting of
*Dekkera bruxellensis, Candida albicans, Candida parapsilosis, Candida pseudointermedia, Saccharomyces cerevisiae, Saccharomycodes ludwigii, Zygosaccharomyces bailii* and *Pichia* sp.,
*Aureobasidium* sp., *Alternaria alternata, Aspergillus brasiliensis, Aspergillus fumigatus, Cladosporium* sp., *Fusarium* sp. *Rhodotorula* sp., *Sporidiobolus* sp., *Sporobolomyces* sp., *Paecilomyces* sp. and *Penicillium* sp.,
further preferably to achieve an antimicrobial effect, preferably for achieving a synergistic antimicrobial effect, against one, more or all germs selected from the group consisting of *S. cerevisiae, Z. bailii, C. albicans, A. pullulans* and *A. brasiliensis*.

What was said above with regard to mixtures preferably to be used according to the invention also applies for preferred embodiments of the contained mixture. The same applies accordingly for preferred embodiments of the preparations to be treated.

Subsequently, the present invention is further illustrated by means of selected examples, without limiting the subject-matter of the present invention thereon. As far as not indicated otherwise, all indications of % relate to the weight (wt.-%).

EXAMPLES

1. *Punica granatum* Extract (GRA):
A pomegranate skin extract is produced by that pomegranates are cut in half and are pressed and the remaining skin rests are subsequently homogenized with warm water at a temperature of 50° C. The mash is subsequently pressed. The obtained extract (filtrate) is subsequently concentrated by distillation.

The obtained, concentrated extract contains, among others, the following components:

| Component | Surface percentage[1] |
|---|---|
| Punicalagin | 14.73 |
| Digalloyl-gallagyl-hexoside | 9.49 |
| Granatin B | 8.24 |
| Punicacortein D | 7.95 |
| Punicacortein A | 5.73 |
| Ellagic acid | 3.09 |

[1]Determination of the surface percentage by UPLC-NQAD

For a subsequent production of single fractions of the concentrated extract, a membrane filtration may for example be applied.

For the production of the membrane filtrates from the pomegranate skin extract, a polyethylene glycol-based flat membrane with a membrane surface of 26 cm$^2$ and a cut-off of 2500 Da was rinsed with ultrapure water at 30 bar and twice for 20 minutes. A 1% extract solution (200 g) was provided in the feed container, heated to 30° C. and impinged with a pressure of 30 bar. After throughput of 138.23 g, it was diluted with 100 g of water and filtered again. The membrane filtrates were lyophilized and a permeate with a yield of 16.8% and a retentate with a yield of 65.8% was obtained.

The obtained fractions were subsequently examined for their components by mass spectrometry. The obtained fractions contain, among others, the following non-volatile components:

| No. | Compound | Molecular formula | Molar mass [Da] | Molecule ion [M − H]$^-$ | Fragmentations [m/z] | $t_R$ [min] |
|---|---|---|---|---|---|---|
| | | Permeate | | | | |
| 1 | Citric acid | $C_6H_8O_7$ | 192 | 191 | 391 | 0.59 |
| 2 | 2,3-(S)-HHDP-D-glucose | $C_{20}H_{18}O_{14}$ | 482 | 481 | 331 | 0.69 |
| 3 | Glucogallin | $C_{13}H_{16}O_{10}$ | 332 | 331 | 125 169 | 1.13 |
| | | Retentate | | | | |
| 1 | Punicalin α | $C_{34}H_{22}O_{22}$ | 782 | 781 | 601, 299, 300 | 1.51 |
| 2 | Punicalagin α | $C_{48}H_{28}O_{30}$ | 1084 | 1083 | 781, 301 | 2.16 |
| 3 | Punicalagin β | $C_{48}H_{28}O_{30}$ | 1084 | 1083 | 781, 301 | 2.67 |
| 4 | Granatin A | $C_{34}H_{24}O_{23}$ | 800 | | 301 | 2.85 |
| 5 | Granatin B | $C_{34}H_{28}O_{27}$ | 925 | 951 | 933, 301 | 4.07 |
| 6 | Ellagic acid | $C_{14}H_6O_8$ | 302 | 301 | | 4.39 |

2. Red Berry Extract—Mixture of *Vaccinium macrocarpon, Vaccinium Angustifolium* and *Fragaria×anapassa* (ROBE):
An extract is produced by that fruits of *Vaccinium macrocarpon, Vaccinium angustifolium* and *Fragaria×anapassa* are mixed and subsequently a filtrate is obtained after pressing. Subsequently, the filtrate (extract) is concentrated by distillation.

The obtained, concentrated extract contains, among others, the following components:

| Components | Surface percentage[1] |
|---|---|
| Quinic acid | 6.94 |
| Cyanidin 3-O-glucoside | 2.59 |
| Avicularin | 2.43 |

-continued

| Components | Surface percentage[1] |
|---|---|
| Quercetin | 2.09 |
| Chlorogenic acid | 2.03 |
| Catechin | 1.86 |
| Peonidin 3-arabinoside | 1.34 |
| Malvidin-3-glucoside | 1.22 |
| Quercetin-3-galactoside | 1.18 |
| (−)-Epicatechin | 1.04 |

[1]Determination of the surface percentage by UPLC-NQAD

3. *Vitis vinifera* Extract (Grape Stone Extract):

An extract is produced by that, at first, grape stones are milled. Then these are extracted with water at 50° C. and filtered to obtain the extract. Subsequently, the obtained extract is concentrated by distillation.

The obtained, concentrated extract contains, among others, the following components:

| Components | Surface percentage[1] |
|---|---|
| Epicatechin | 9.05 |
| Catechin | 8.41 |
| Procyanidin B2 | 5.45 |
| Epicatechin gallate | 5.17 |
| Procyanidin B4 | 4.5 |
| Gallic acid | 3 |
| Procyanidin C1 | 2.61 |
| 3-Galloylprocyanidn B2 | 2.53 |

[1]Determination of the surface percentage by UPLC-NQAD

For a subsequent production of single fractions of the concentrated extract, a membrane filtration may for example be applied.

For the production of the membrane filtrates from the grape stone extract, a polyethylene glycol-based flat membrane with a membrane surface of 26 cm$^2$ and a cut-off of 2500 Da was rinsed with ultrapure water at 30 bar and twice for 20 minutes. A 1% extract solution (200 g) was provided in the feed container, heated to 30° C. and impinged with a pressure of 30 bar. After throughput of 138.23 g, it was diluted with 100 g of water and filtered again. The membrane filtrates were lyophilized and a permeate with a yield of 7.6% and a retentate with a yield of 58.8% was obtained.

Alternatively or additionally, a polar and a nonpolar fraction can be obtained, e.g. by means of chromatographic methods.

For the production of a polar and an unipolar fraction, a solution of 100 mg grape stone extract in 1 mL deionized water was produced and applied on the preparative HPLC column (PRP-1 column 250×21.5 mm; 10 μm particle size) which was preconditioned with water/ethanol (90/10) at a flow rate of 10 ml/minute. Deionized water and ethanol (99.5%) were used as solvent at an oven temperature (60° C. isotherm). First, it was eluted for 25 min with water/ethanol (90/10). Afterwards, the ethanol proportion was increased within ten minutes by ten percent to 20% and was kept at a constant level for 10 minutes. Subsequently, the ethanol proportion was increased to 100% within five minutes and maintained for five minutes. The polar fraction was collected at a run-time of from 10 to 36 minutes and the unipolar fraction was collected at a run-time of from 37 to 55 minutes. The yield of the polar fraction was 48% and the yield of the unipolar fraction was 28%.

The obtained fractions were subsequently examined for their components by mass spectrometry. The obtained fractions contain, among others, the following non-volatile components:

| No. | Compound | Molecular formula | Molar mass [Da] | Molecule ion [M − H]$^-$ | Fragmentations [m/z] | $t_R$ [min] |
|---|---|---|---|---|---|---|
| | | Permeate | | | | |
| 1 | Gallic acid | $O_7H_6O_5$ | 170 | 169 | 125 | 1.12 |
| 2 | (−)-Catechin | $C_{15}H_{14}O_6$ | 290 | 289 | 245, 205, 179 | 2.75 |
| 3 | (−)-Epicatechin | $C_{15}H_{14}O_6$ | 290 | 289 | 245, 205, 179 | 3.17 |
| 4 | (−)-Epicatechin 3-O-gallat | $C_{22}H_{18}O_{10}$ | 442 | 441 | 331, 289, 271, 169 | 4.21 |
| | | Retentate | | | | |
| 1 | Gallic acid | $O_7H_6O_5$ | 170 | 169 | 125 | 1.08 |
| 2 | Procyanidin C2 | $C_{45}H_{38}O_{18}$ | 866 | 865 | 739, 713, 695, 575, 407, 289 | 1.69 |
| 3 | (−)-Catechin | $C_{14}H_{14}O_6$ | 290 | 289 | 245, 205, 179 | 2.66 |
| 4 | Procyanidin B1 | $C_{30}H_{26}O_{12}$ | 578 | 577 | 425, 289 | 2.76 |
| 5 | Procyanidin C1 | $C_{45}H_{38}O_{18}$ | 866 | 865 | 577, 575, 425, 407 | 2.88 |
| 6 | Procyanidin B3 | $C_{30}H_{26}O_{12}$ | 578 | 577 | 425, 289 | 2.97 |
| | Procyanidin B2 | $C_{30}H_{26}O_{12}$ | 578 | 577 | 425, 289 | 3.07 |
| 7 | (−)-Epicatechin | $C_{15}H_{16}O_6$ | 290 | 289 | 245, 205, 179 | 3.15 |
| 8 | Procyanidin B-gallat | $C_{37}H_{30}O_{16}$ | 730 | 729 | 577, 289 | 3.93 |
| 9 | (−)-Epicatechin 3-O-gallat | $C_{22}H_{18}O_{10}$ | 442 | 441 | 289, 271, 169 | 4.28 |
| 10 | Procyanidin B5 | $C_{30}H_{26}O_{12}$ | 578 | 577 | 425, 289, 125 | 4.49 |
| | | Polar fraction | | | | |
| 1 | (−)-Catechin | $C_{15}H_{14}O_6$ | 290 | 289 | 245, 205, 179 | 2.54 |
| 2 | Procyanidin B1 | $C_{30}H_{26}O_{12}$ | 578 | 577 | 451, 289 | 2.58 |
| 3 | Procyanidin C1 | $C_{45}H_{38}O_{18}$ | 866 | 865 | 713, 695, 577, 575, 425, 407, 289 | 2.83 |
| 4 | Procyanidin B3 | $C_{30}H_{26}O_{12}$ | 578 | 577 | 425, 289 | 2.95 |

-continued

| No. | Compound | Molecular formula | Molar mass [Da] | Molecule ion [M − H]⁻ | Fragmentations [m/z] | $t_R$ [min] |
|---|---|---|---|---|---|---|
| 5 | Procyanidin B2 | $C_{30}H_{26}O_{12}$ | 578 | 577 | 425, 289 | 3.06 |
| 8 | (−)-Epicatechin | $C_{15}H_{14}O_6$ | 290 | 289 | 245, 205, 179 | 3.17 |
| 9 | Procyanidin B-gallat | $C_{37}H_{30}O_{16}$ | 730 | 729 | 577, 289 | 3.44 |
| 10 | Procyanidin C | $C_{45}H_{38}O_{18}$ | 866 | 865 |  | 3.51 |
| Nonpolar fraction ||||||| 
| 1 | (−)-Catechin | $C_{15}H_{14}O_6$ | 290 | 289 | 245, 205, 179 | 2.49 |
| 2 | (−)-Epicatechin | $C_{15}H_{14}O_6$ | 290 | 289 | 245, 205, 179 | 3.13 |
| 3 | Procyanidin B-gallate | $C_{37}H_{30}O_{18}$ | 730 | 729 | 577, 289 | 3.60 |
| 4 | Procyanidin C | $C_{45}H_{38}O_{18}$ | 866 | 865 | 577, 425, 407, 289 | 3.76 |
| 5 | Procyanidin B-gallate | $C_{37}H_{30}O_{16}$ | 730 | 729 | 577, 289 | 3.86 |
| 6 | Procyanidin B7 | $C_{30}H_{28}O_{12}$ | 578 | 577 | 407, 289, 125 | 3.94 |
| 7 | (−)-Epicatechin 3-O-gallat | $C_{22}H_{18}O_{10}$ | 422 | 441 | 289, 271, 169 | 4.24 |
| 8 | Procyanidin B5 | $C_{30}H_{26}O_{12}$ | 578 | 577 | 425, 289, 125 | 4.31 |
| 9 | Procyanidin C | $C_{45}H_{38}O_{18}$ | 866 | 865 |  | 4.43 |
| 10 | Procyanidin B-gallate | $C_{37}H_{30}O_{16}$ | 730 | 729 | 575, 289, 125 | 5.34 |

4. Examination of the Antimicrobial Effect of Different Extracts:

For the examination of the antimicrobial effect of different extracts alone, i.e. without a combination with component (B) according to the invention, exemplary extracts such as described in Examples 1 to 3 were used. For this purpose, the extracts were dissolved in citrate buffer at a pH of 3 and with 500 mg/kg. The samples were inoculated with $5.63 \times 10^4$ CFU/mL *S. cerivisiae*, $1.89 \times 10^4$ *Z. bailii* and $3.75 \times 10^4$ *C. albicans*.

*C. albicals* resisted the extracts over the 21 days.

*A. pullulans* could be reduced during the 28 days. A 100% reduction could be observed for GRA after 28 days.

*A. brasiliensis* could be detected with lower germination number after 28 days.

As shown by the results below (cf. Example 7), the antimicrobial effectiveness of the extracts can be improved by combination with a component (B) as described herein.

|  | Inoculum (CFU/mL) | Amount of CFU/mL after day ||||| 
|---|---|---|---|---|---|---|
|  |  | 1 | 7 | 14 | 21 | 28 |
| *S. cerivisiae* |||||||
| ROBE | $5.63 \times 10^4$ | $1.0 \times 10^3$ | 0 | 0 | 0 | 0 |
| GRA | $5.63 \times 10^4$ | $4.0 \times 10^4$ | 0 | 0 | 0 | 0 |
| *Z. bailii* |||||||
| ROBE | $1.89 \times 10^4$ | $4.0 \times 10^3$ | $1.0 \times 10^2$ | 0 | 0 | 0 |
| GRA | $1.89 \times 10^4$ | $4.0 \times 10^2$ | $7.0 \times 10^1$ | 0 | 0 | 0 |
| *C. albicans* |||||||
| ROBE | $3.75 \times 10^4$ | $4.0 \times 10^3$ | $4.0 \times 10^4$ | $4.0 \times 10^4$ | $4.0 \times 10^4$ | $7.0 \times 10^4$ |
| GRA | $3.75 \times 10^4$ | $1.0 \times 10^3$ | $4.0 \times 10^3$ | $4.0 \times 10^3$ | $3.3 \times 10^3$ | $7.0 \times 10^3$ |
| *A. pullulans* |||||||
| ROBE | $2.5 \times 10^4$ | $7.0 \times 10^2$ | $4.0 \times 10^1$ | $4.0 \times 10^4$ | $1.0 \times 10^3$ | $4.0 \times 10^2$ |
| GRA | $2.5 \times 10^4$ | $1.0 \times 10^2$ | $7.0 \times 10^1$ | $7.0 \times 10^2$ | $7.0 \times 10^1$ | 0 |
| *A. brasiliensis* |||||||
| ROBE | $1.0 \times 10^4$ | $3.7 \times 10^3$ | $7.0 \times 10^1$ | $1.0 \times 10^2$ | $4.0 \times 10^1$ | $4.0 \times 10^1$ |
| GRA | $1.0 \times 10^4$ | $7.0 \times 10^1$ | $3.7 \times 10^2$ | $1.0 \times 10^2$ | $4.0 \times 10^1$ | $3.7 \times 10^2$ |

With regard to *S. cerevisiae*, lower germination numbers were observed after 24 g incubation time. After 7 days, the growth ceased.

With regard to *Z. bailii*, lower germination numbers were observed after 7 days and starting with 14 days, no new colony formation has taken place.

5. Further Examination on the Antimicrobial Effect of Selected Extracts and Fractions Thereof:

For further examination of the antimicrobial effect of different extracts alone, i.e. without a combination with component (B) or fractions thereof according to the invention, exemplary extracts or fractions thereof such as described in Examples 1 to 4 were used. The extracts or, respectively, fractions thereof were dissolved in citrate buffer at a pH of 5 and in a dose as indicated in the table. The samples were inoculated with $3.8 \times 10^4$ CFU/mL S. cerivisiae.

| Extract/Fraction | Dose [mg/kg] | Germination number S. cerevisiae after inoculation | Germination number S. cerevisiae after 28 days |
|---|---|---|---|
| Vitis vinifera extract | 500 | 3.80E+04 | 7.00E+02 |
| Vitis vinifera polar fraction | 250 | 3.80E+04 | 7.00E+03 |
| Vitis vinifera nonpolar fraction | 200 | 3.80E+04 | 7.00E+01 |
| Vitis vinifera membrane filtrate <2500 Da fraction (permeate) | 200 | 3.80E+04 | 4.00E+03 |
| Vitis vinifera membrane filtrate >2500 Da fraction (retentate) | 200 | 3.80E+04 | 7.00E+02 |
| Punica granatum extract | 500 | 3.80E+04 | 4.00E+03 |
| Punica granatum membrane filtrate <2500 Da fration (permeate) | 100 | 3.80E+04 | 1.00E+04 |
| Punica granatum membrane filtrate >2500 Da fraction (retentate) | 200 | 3.80E+04 | 1.00E+02 |
| Negative control without addition | 0 | 3.80E+04 | 4.00E+03 |
| Positive control potassium sorbate | 375 | 3.80E+04 | 1.00E+03 |

The negative control did not result in a significant reduction of the germination number.

However, the positive control with 375 mg/kg potassium sorbate also did not show a significant reduction in the germination number. The underlying reason is on the one side that in comparison to pH 3 as in application example table 2, sorbic acid is only in a small extent present in its effective non-dissociated form and the optimal growth of S. cerevisiae between pH 4 and 6 does occur at pH 5.

For the Punica granatum extract (and for the Vitis vinifera extract) no significant reduction in the germination number of S. cerevisiae can be observed. It was thus even more surprising that by fractionation of the extracts, an inhibition of the antimicrobial growth, i.e. reduction of the germination number by log 2 could be observed. Thus, the germination number was significantly reduced by addition of 200 mg/kg of the non-polar fraction of Vitis vinifera extract and by addition of 200 mg/kg Punica granatum membrane filtrate >2500 Da.

As is shown by the below results (cf. Example 7), the antimicrobial effectiveness of the extracts can be improved by combination with a component (B) as described herein.

6. Interaction of Extracts and Flavouring Agents:

| Basis | Composition | Smell | Taste |
|---|---|---|---|
| Drink with cherry taste (produced by 1 part syrup and 4 parts water) | Without addition | Fruity, cherry | Sweet, slightly sour, juicy |
| | 200 ppm GRA (Ex. 1) | Less cherry, less fruity, fatty, rancid, stodgy | Sweet, more sour than basis, slightly astringent |
| | 200 ppm GRA (Ex. 1) +100 ppm Vanillic acid, +1 ppm Benzaldehyde | Cherry, fruity, fatty | Sweet, more juicy than basis |
| | 200 ppm grape stone extract (Ex. 3) | Less cherry, less fruity | Sweet, more sour than basis, astringent |
| | 200 ppm grape stone extract (Ex. 3) +100 ppm Vanillic acid, +1 ppm Benzaldehyde | Fruity, cherry | Sweet, slightly sour, more juicy than basis, little astringent |
| | 200 ppm ROBE (Ex. 2) | Fruity, cherry | Sweet, more sour than basis, slightly metallic |
| | 200 ppm ROBE (Ex. 2) +100 ppm Vanillic acid, +1 ppm Benzaldehyde | Fruity, cherry | Sweet, juicy |
| Beer mixed drink with grapefruit taste, less than 0.1 Vol. % alcohol | Without addition | Grapefruit, yeasty, fruity | Bitter after-taste, sour |
| | 200 ppm GRA (Ex. 1) +100 ppm Vanillic acid +20 ppm Homoeriodictyol +5 ppm Hesperitin | Grapefruit, fruity | Less bitter than basis, more full-bodied |
| | 200 ppm grape stone extract (Ex. 3) +100 ppm Vanillic acid +20 ppm Homoeriodictyol +5 ppm Hesperitin | Grapefruit, more fruity than basis | Slightly bitter, juicy |

-continued

| Basis | Composition | Smell | Taste |
|---|---|---|---|
| | 200 ppm ROBE (Ex. 2) +100 ppm Vanillic acid +20 ppm Homoeriodictyol +5 ppm Hesperitin | Grapefruit, fruity | Slightly bitter, juicy |
| Tomato ketchup | Without addition | Vinegar, pungent, tomato, carnation-like | Sour, stinging, sweet |
| | 500 ppm grape stone extract (Ex. 3) +5 ppm Hop extract +20 ppm Pellitorin | Vinegar, tomato, carnation-like | Sweet slightly less sour |
| | 500 ppm ROBE (Ex. 2) +5 ppm Hop extract +20 ppm Pellitorin | Vinegar, tomato, carnation-like | Less sour, stinging, sweet |
| Salad cream with 55% water | Without addition | Egg, fatty, slightly vinegar | Fatty, sour, pungent mustard |
| | 500 ppm grape stone extract (Ex. 3) +200 ppm lactic acid +0.1 ppm Geranial +0.1 ppm Neral | Egg, fatty, slightly vinegar | Fatty, slightly more sour, less pungent mustard, slightly nutty |

The Examples show that by addition of distinct flavouring agents, the sensory impression of the product, to which the above-mentioned extracts were added, is improved while maintaining product-specific olfactory and gustatory notes. It has been found that undesired side-notes of the plant extracts such as bitter, astringent, metallic can be transferred into attributes which are sensorially perceived as positive such as more juicy, more full-bodied, sweeter and more complex when combined with the flavouring agents. The same applies accordingly to the combination of fractions of such extracts as described herein with the flavouring agents as described herein. For optimizing the desired effect, a skilled person may test and use different doses, depending on the matrix.

For a further test, still water, composed of 60 mg/kg Acesulfame-K, 60 mg/kg Sucralose, 0.15 g/100 g citric acid, 200 mg/kg GRA (Ex. 1) and 0.1 g/100 g cherry flavouring, was used. Flavouring agents and mixtures of flavouring agents with the effect described below were added and compared with the sensory profile of the basis without addition:

| Addition of flavouring agent | Dose | Sensory effect compared to basis |
|---|---|---|
| Eriodictyol | 10 mg/kg | Less benzaldehyde, more like ripe cherry, less astringent |

-continued

| Addition of flavouring agent | Dose | Sensory effect compared to basis |
|---|---|---|
| Hesperitin | 25 mg/kg | Stronger like juicy cherry |
| Mogroside | 10 mg/kg | More complex in the taste, more mouthfill |
| Matairesinol | 10 mg/kg | More fresh, more citric, less lingering |
| Pellitorin | 10 mg/kg | More intensive cherry |
| Steviolglycosides | 10 mg/kg | More complex in the taste, more mouthfill |
| Vanillic acid | 100 mg/kg | More balanced, less sour |

In the scope of a further test, the antimicrobial effect of aroma and extract combinations was examined. The following table shows the results of a germ load test, analogous to the experiments of Examples 5 and 6, with the difference that the mixture was produced with pure water at a pH of 7. For example, grape stone extract and the flavouring agent vanillic acid have a different effect against yeasts. In the combination, however, also an effect against fungi and an optimal effect against yeasts was observed. The pomegranate and red berry extract have a lower effect at pH 7 compared to pH 3 (cf. Example 5), the pomegranate extract eliminates S. cerevisiae in less than 14 days at 1000 mg/kg. In combination with Limonene-containing lemon oils, however, the effect can be increased for higher pH values.

| Component | Concentration in sample | S. cerevisiae | Z. bailii | C. albicans | A. pullulans | A. brasiliensis |
|---|---|---|---|---|---|---|
| | | Antimicrobial activity against the germs at pH 7 | | | | |
| Grape stone extract (Ex. 3) | 400 ppm | Elimination in less than 24 hours | Elimination in less than 7 days | | | |
| Vanillic acid | 400 ppm | Elimination in less than 14 days | Elimination in less than 24 hours | Elimination in less than 24 hours | | |
| Grape stone extract (Ex. 3) + Vanillic acid | 400/400 ppm | Elimination in less than 24 hours | Elimination in less than 24 hours | Elimination in less than 24 hours | Reduction by at least log2 | Reduction by at least log2 |
| GRA (Ex. 1) | 1000 ppm | Elimination in less than 14 days | | | | |

-continued

| Component | Concentration in sample | S. cerevisiae | Z. bailii | C. albicans | A. pullulans | A. brasiliensis |
|---|---|---|---|---|---|---|
| | | Antimicrobial activity against the germs at pH 7 | | | | |
| Lemon oil 25x terpene reduced[1] + GRA (Ex. 1) | 100 ppm + 400 ppm | Elimination in less than 14 days | Elimination in less than 24 hours | Elimination in less than 7 days | | |
| Lemon oil[1] + GRA (Ex. 1) | 200 ppm + 400 ppm | Elimination in less than 7 days | Elimination in less than 7 days | Reduction by at least log2 | Elimination in less than 14 days | Reduction by at least log2 |
| Lemon oil terpenes[1] + ROBE (Ex. 2) | 200 ppm + 400 ppm | Elimination in less than 14 days | Elimination in less than 14 days | Elimination in less than 7 days | | |

[1]the amount of Limonene of the lemon oils is in a range of from 70% to 1%.

7. Application Examples:

The mixtures or, respectively, combinations to be used according to the invention can be applied to a plurality of preparations. For example it is referred to the following possibilities of application (instead of the exemplarily mentioned extracts, also other extracts or fractions thereof as described herein can be applied):

| Ratio (Weight) | Component (A) | Ratio (Weight) | Component (B) | Application |
|---|---|---|---|---|
| 2.5 | Extract of *Punica granatum* (e.g. GRA of Ex. 1) | 1 | Vanillic acid | Still drinks |
| 20 | Extract mixture of *Vaccinium macrocarpon*, *Vaccinium myrtillus* and *Vaccinium vitis-idaea* | 1 | Hesperetin | Ketchup |
| 30 | Extract mixture of *Vitis vinifera* and *Humulus lupulus* | 1 | Pellitorin | Salad cream |
| 3 | Extract of *Vitis vinifera* (e.g. of Example 3) | 1 | Vanillic acid | Drink syrup |

7.1 Drink with Cherry Taste (Sugar-Free):

| Component | Wt.-% |
|---|---|
| Water | 99.73 |
| Citric acid | 0.13 |
| Cherry flavouring | 0.1 |
| Extract of *Punica granatum*[1] | 0.02 |
| Vanillic acid | 0.01 |
| Acesulfame K | 0.006 |
| Sucralose | 0.006 |

[1]The extract contains 8.3 g/kg Ellagic acid and 4.7 g/kg gallic acid 7.2 Drink with Cherry Taste (Sugar-Containing):

| Component | Wt.-% |
|---|---|
| Water | 91.74 |
| Zucker | 8 |
| Citric acid | 0.13 |
| Cherry flavouring | 0.1 |
| Extract of *Punica granatum*[1] | 0.02 |
| Vanillic acid | 0.01 |

[1]The extract contains 8.3 g/kg Ellagic acid and 4.7 g/kg gallic acid 7.3 Beer Mixed Drink with Grapefruit Taste (<0.1 Vol. % Alc.):

| Component | Wt.-% |
|---|---|
| Wheat beer alcohol-free (consisting of water, wheat malt, barley malt, hop extract, yeast) | 50.00 |
| Fruit soft drink (consisting of water, fruit juice (5.5%), sugar, fruit juice concentrates, carbonic acid, fruit extracts, citric acid, ascorbic acid, stabilizer locust bean gum) | 49.97 |
| Grape stone extract[1] | 0.02 |
| Homoeriodictyol | 0.01 |

[1]The extract contains 10.3 g/kg gallic acid 7.4 Alcohol-Free Malt Drink (<0.1 Vol. % Alc.):

| Component | Wt.-% |
|---|---|
| Water | 95.88 |
| Malt flavouring | 4.00 |
| Citric acid water-free | 0.08 |
| Grape stone extract[1] | 0.02 |
| Homoeriodictyol | 0.01 |

[1]The extract contains 10.3 g/kg gallic acid 7.5 Tomato Ketchup:

| Component | Wt.-% |
|---|---|
| Water | 37.23 |
| Tomato puree double concentrated | 23.5 |
| sugar | 20 |
| Vinegar 5% | 16 |
| Salt | 3 |
| Spice and herb extract | 0.1 |
| Red berry extract[1] | 0.05 |
| Pepper | 0.05 |
| Pellitorin | 0.002 |

[1]the extract contains 2.2 g/kg chlorogenic acid 7.6 Salad Cream (Approx. 55 wt. % Water):

| Component | Wt.-% |
|---|---|
| Edible oil | 37.00 |
| Water | 38.58 |
| Vinegar 5% | 12 |
| Citric acid 50% in water | 0.8 |
| Sugar | 3.7 |
| Egg yolk | 3.0 |
| Salt | 2.0 |

-continued

| Component | Wt.-% |
|---|---|
| Starch | 1.5 |
| Skimmed milk powder | 0.7 |
| Onion powder | 0.5 |
| Spices | 0.1 |
| Hop extract[1] | 0.0001 |
| Lactic acid | 0.02 |
| Cream-Milk flavouring Contains, among others, decalactone delta, dodecalactone delta, acetyl methyl carbinol, dimethyl disulfide | 0.05 |

[1] the extract contains 8.1 g/kg chlorogenic acid

The invention claimed is:

1. A method for prolonging the durability of a perishable foodstuff by inhibiting growth of *S. cerevisiae, Z. bailii, A. pullulans, A. brasiliensis*, or a combination thereof, the method comprising:
(I) adding to a foodstuff susceptible to microbial growth of *S. cerevisiae, Z. bailii, A. pullulans, A. brasiliensis*, or a combination thereof, a synergistically effective amount of an antimicrobial mixture, the antimicrobial mixture comprising:
    (a) an extract from peels of *Punica granatum* comprising one or more compounds selected from catechins, chlorogenic acid, p-coumaric acid, epicatechin, ellagic acid, gallic acid, caffeic acid, sinapinic acid, and cinnamic acid, or combinations thereof; and
    (b) lemon oil comprising limonene; and
(II) synergistically inhibiting the microbial growth of the *S. cerevisiae, Z. bailii, A. pullulans, A. brasiliensis*, or combination thereof, and prolonging the durability of the perishable foodstuff,
    wherein the antimicrobial mixture of (a) and (b) is synergistically effective against the *S. cerevisiae, Z. bailii, A. pullulans, A. brasiliensis*, or combination thereof, compared to the individual activity of (a) and the individual activity of (b).

2. The method of claim 1, wherein the method synergistically inhibits the microbial growth of *S. cerevisiae*.

3. The method of claim 1, wherein the method synergistically inhibits the microbial growth of *Z. balii*.

4. The method of claim 1, wherein the method synergistically inhibits the microbial growth of *A. pullulans*.

5. The method of claim 1, wherein the method synergistically inhibits the microbial growth of *A. brasiliensis*.

6. The method according to claim 1, wherein a ratio of a total amount of (a) to a total amount of (b) is 10:1 to 1:1 ((a):(b)).

7. The method according to claim 1, wherein the preparation is a drink.

8. The method according to claim 1, wherein the drink has a pH of from 3 to 7.

9. A method for prolonging the durability of a perishable foodstuff by inhibiting growth of *S. cerevisiae, Z. bailiff, C. albicans, A. pullulans, A. brasiliensis*, or a combination thereof, the method comprising:
(I) adding to a foodstuff susceptible to microbial growth of *S. cerevisiae, Z. bairn, C. albicans, A. pullulans, A. brasiliensis*, or a combination thereof, a synergistically effective amount of an antimicrobial mixture, the antimicrobial mixture comprising:
    (a) an extract from *Vitis vinifera* comprising one or more compounds selected from Epicatechin, Catechin, Procyanidin B2, Epicatechin gallate, Procyanidin B4, Gallic acid, Procyanidin C1,3-Galloylprocyanidin B2; and
    (b) vanillic acid; and
(II) synergistically inhibiting the microbial growth of the *S. cerevisiae, Z. bailii, C. albicans, A. pullulans, A. brasiliensis*, or combination thereof, thereby prolonging the durability of the perishable foodstuff,
    wherein the antimicrobial mixture of (a) and (b) is synergistically effective against the *S. cerevisiae, Z. bailii, C. albicans, A. pullulans, A. brasiliensis*, or combination thereof, compared to the individual activity of (a) and the individual activity of (b).

10. The method of claim 9, wherein the method synergistically inhibits the microbial growth of *S. cerevisiae*.

11. The method of claim 9, wherein the method synergistically inhibits the microbial growth of *Z. balii*.

12. The method of claim 9, wherein the method synergistically inhibits the microbial growth of *C. albicans*.

13. The method of claim 9, wherein the method synergistically inhibits the microbial growth of *A. pullulans*.

14. The method of claim 9, wherein the method synergistically inhibits the microbial growth of *A. brasiliensis*.

15. The method according to claim 9, wherein a ratio of a total amount of (a) to a total amount of (b) is 10:1 to 1:1 ((a):(b)).

16. The method according to claim 9, wherein the preparation is a drink.

17. The method according to claim 9, wherein the drink has a pH of from 3 to 7.

* * * * *